United States Patent
Blommel et al.

[11] Patent Number: 5,962,755
[45] Date of Patent: *Oct. 5, 1999

[54] PROCESS FOR THE ISOMERIZATION OF BENZENE CONTAINING FEED STREAMS

[75] Inventors: Paul George Blommel, Bolingbrook; Christopher David Gosling, Roselle; Steve A. Wilcher, Wilmette, all of Ill.

[73] Assignee: Uop LLC, Des Plaines, Ill.

[*] Notice: This patent is subject to a terminal disclaimer.

[21] Appl. No.: 09/094,248

[22] Filed: Jun. 9, 1998

Related U.S. Application Data

[63] Continuation-in-part of application No. 08/748,225, Nov. 12, 1996, Pat. No. 5,763,713.
[51] Int. Cl.[6] ............................. C07C 5/22; C07C 1/13; C07C 5/10
[52] U.S. Cl. ..................... 585/253; 585/263; 585/266; 585/750; 585/258; 585/734
[58] Field of Search .................. 585/253, 258, 585/263, 734, 750, 266

[56] References Cited

U.S. PATENT DOCUMENTS

| | | | |
|---|---|---|---|
| 4,783,575 | 11/1988 | Schmidt et al. | 585/748 |
| 5,003,118 | 3/1991 | Low et al. | 585/253 |
| 5,763,713 | 6/1998 | Blommel et al. | 585/253 |

*Primary Examiner*—Glenn Caldarola
*Assistant Examiner*—Thuan D. Dang
*Attorney, Agent, or Firm*—Thomas K. McBride; John G. Tolomei

[57] ABSTRACT

A process for saturating benzene in a light paraffin isomerization process can accommodate varying quantities of benzene through the incorporation of progressive steps that control temperatures in the isomerization zone while performing a majority of the saturation within an immediately upstream benzene saturation zone. The process is suited for saturating benzene to very low levels while feedstream concentrations of benzenes may vary from 2 to 25 wt % throughout a given period of operation. The process can accommodate rapid swings in benzene concentration that may occur on a daily basis. The invention is particularly suited for the use of a sulfated zirconia catalyst that allows the utilization of existing reactor vessels in an isomerization process.

6 Claims, 4 Drawing Sheets

PROCESS FOR THE ISOMERIZATION OF BENZENE CONTAINING FEED STREAMS

CROSS-REFERENCE TO RELATED APPLICATIONS

This application is a continuation-in-part of U.S. Ser. No. 08/748,225 that was filed Nov. 12, 1996, and issued as U.S. Pat. No. 5,763,713.

FIELD OF THE INVENTION

The present invention relates to the isomerization of feedstreams containing $C_4$–$C_6$ paraffins and benzene.

BACKGROUND OF THE INVENTION

Recent concerns about volatility and toxicity of hydrocarbon fuel and the resultant environmental damage has made it desirable to limit the content and composition of aromatic hydrocarbons in such fuels and benzene in particular. Limiting benzene poses some of the most severe problems for the operation of catalytic reformers that have been relied on to raise the octane of unleaded fuels. Reformers that were typically operated at high severity to produce high octane benzene and aromatic hydrocarbons must now be operated to eliminate benzene and reduce aromatics. There are a variety of ways in which the operation of the reforming section may be altered to reduce the reformate benzene concentration. Changing the cut point of the naphtha feed split between the reforming and isomerization zones from 180 to 200° F. will remove benzene, cyclohexane and methylcyclopentane from the reformer feed. Benzene can alternately also be removed from the reformate product by splitting the reformate into a heavy fraction and a light fraction that contains the majority of the benzene. Practicing either method will put a large quantity of benzene into the feed to other processing units, particularly the isomerization zone. Therefore, it is still necessary to have an efficient and cost effective means for removing benzene from feeds.

Octane improvement is also obtained by catalytically isomerizing the $C_4$–$C_6$ paraffins hydrocarbons to rearrange the structure of the paraffinic hydrocarbons into branch-chained paraffins. Increasing amounts of the benzene that were formerly blended with finished gasoline products to increase octane are present in the isomerization feeds. It is known from U.S. Pat. No. 5,003,118 to saturate benzene in such feedstocks by the use of separate saturation zone upstream of the isomerization zone and that heat evolved from the saturation reaction can be used to heat the feed to the isomerization zone. As the benzene concentration of the feed varies, saturation of high benzene feeds can generate high heat inputs that excessively raise temperatures. High temperatures in the isomerization zone shift the equilibrium away from the production of the desired isoparaffins. Large changes in the concentration of benzene that are now often encountered when isomerizing light hydrocarbons make stable operation of isomerization processes difficult. Depending on the source of feed and the particular refining application benzene concentration can change by 20% or more on a daily basis.

The saturation of benzene in the feedstream also produces cyclohexane. U.S. Pat. No. 4,783,575 teaches the opening of cyclo-paraffinic rings in conjunction with the isomerization of light hydrocarbons using a platinum alumina catalyst. The opening of the cyclo-paraffnic rings increases the available paraffins for isomerization to $C_6$ isoparaffins and provides further octane upgrading. Consequently, processes are sought for the elimination of benzene and the decyclization of the resulting saturated cyclic hydrocarbons that can accommodate widely varying quantities of benzene in the feed.

BRIEF DESCRIPTION OF THE INVENTION

This invention is a process for saturating widely varying quantities of benzene in a light paraffin isomerization feed stream. The invention uses a combination of feed and product splitting between an integrated benzene saturation and paraffin isomerization reaction zone along with progressive by passing of the saturation zone heat exchange to control temperatures in the isomerization zone while saturating light paraffin isomerization feeds that may contain from 2 to 30 wt % benzene. While the benzene concentration remains at relatively low levels, less than about 10 wt %, unfavorable increases in the isomerization zone temperature are prevented through the by passing of a portion of the feed to the saturation zone around the feed exchanger that recovers heat from the isomerization zone effluent. As the benzene concentration increases unfavorable increases in the isomerization temperature are further avoided by splitting a stream from the feed, the isomerization zone effluent or both and charging the split stream portion directly to the isomerization zone. The portion directly charged to the isomerization zone operates as a quench that further controls temperature in the isomerization reaction zone.

Accordingly in one embodiment this invention is a process for the hydrogenation of benzene and the isomerization of $C_4$ to $C_6$ paraffins that passes at least a portion of a feedstream comprising benzene and $C_4$ to $C_6$ paraffins and a hydrogen containing stream to a benzene saturation zone and into contact with a benzene saturation catalyst at benzene saturation conditions to produce an intermediate stream containing cyclohexane. The intermediate stream passes to an isomerization zone and contacts an isomerization catalyst at isomerization conditions to increase the isoparaffin content of the intermediate stream and produce an isomerization zone output stream. A quench stream comprising at least a portion of one of the feedstream or the output stream passes directly into the isomerization zone when the benzene content of the feedstream is 5 wt % or more. An isomerization effluent stream comprising at least a portion of the output stream is recovered.

In another embodiment this invention is a process for the hydrogenation and decyclization of benzene and the isomerization of C4 to C6 paraffins from a hydrocarbon feedstream having a concentration of benzene that fluctuates between above and below 5 wt %. The method passes at least a portion of a feedstream comprising benzene and $C_4$ to $C_6$ paraffins and a hydrogen containing stream to a benzene saturation zone and into contact with a benzene saturation catalyst at benzene saturation conditions to produce an intermediate stream containing cyclohexane. The intermediate stream passes to an isomerization zone inlet and contacts the intermediate stream with an isomerization catalyst at isomerization conditions in the isomerization zone to decyclize the cyclohexane, increase the isoparaffin content of the intermediate stream and produce an isomerization zone output stream. At least a portion of the isomerization zone output stream passes into indirect heat exchange with a portion of the feedstream entering the saturation zone. The isomerization zone output stream passes to a separator to recover hydrogen and an isomerization zone effluent stream. At least a portion of said hydrogen is recycled to the saturation zone. The temperature at the inlet of the isomerization zone is maintained below about 350° F. by charging a portion of the feedstream directly to the saturation zone without the indirect heat exchange as long as the benzene concentration in the feedstream is below 5 wt % and passing a quench stream comprising at least a portion of one of said feedstream or said isomerization zone effluent stream directly into said isomerization zone when the benzene content of said feedstream exceeds 5 wt %.

The process can be operated to produce isomerization products having benzene concentrations or less than 0.1 wt %. More preferably the process is operated to produce an essentially complete saturation of benzene. The upstream benzene saturation zone will be the primary location for the saturation of the benzene however saturation of the remaining benzene will take place in the isomerization zone. Therefore it will still be possible to attain very low benzene concentration while controlling isomerization temperature by directing a portion of the isomerization zone feed directly into the isomerization zone.

This invention also utilizes the heat of reaction from the benzene saturation zone to save external heat input to the system. The benzene saturation zone heats the intermediate feed stream that enters the reaction zone. As heat evolution in the benzene saturation zone increases with the increasing amount of benzene in the feed, by passing of the feed heat exchanger with a portion of the feed to the saturation zone keeps the temperature of the intermediate stream down as it absorbs more heat in the saturation zone. Directing the feed or the separated isomerization zone effluent into the isomerization zone provides additional direct temperature control as temperatures in the saturation zone continue to increase with further increasing benzene content. With sufficient benzene content, heat generated from the saturation zone can completely eliminate the need for external heat input. In addition to the feed or intermediate streams other external diluent fluids may pass to the isomerization zone to further control the isomerization zone temperature.

A particularly beneficial method of practicing this invention uses a sulfated zirconia catalyst. Along with good isomerization activity, sulfated zirconia catalysts have good benzene saturation activity along with excellent activity for opening the rings of the cyclohexane. The sulfated zirconia catalyst also has a higher density than other traditional alumina and zeolite based isomerization catalysts. This higher density is especially advantageous for retrofitting existing isomerization zones for the practice of this invention. Since, relative to other solid isomerization catalyst, less sulfated zirconia catalyst is needed to maintain the same activity, a substantial portion of the reactor volume that was formerly needed for catalyst is made available for the incorporation of a saturation reaction zone upstream of an isomerization zone in the same reaction vessel. Thus, a single isomerization zone vessel may be revamped for operation in accordance with this invention without sacrificing any isomerization activity by loading a sulfated zirconia catalyst into the reaction zone and using the additional reactor volume to provide a saturation zone.

Other embodiments, aspects and details of this invention are disclosed in the following detailed description of the invention.

DETAILED DESCRIPTION OF THE INVENTION

The advantages of this invention in obtaining a high benzene conversion with controlled temperatures is applicable to a variety of feedstreams. Suitable feedstocks for this invention will generally include $C_4$ plus hydrocarbons up to an end boiling point of about 250° C. (482° F.). The feedstocks that are used in this invention will typically include hydrocarbon fractions rich in $C_4$–$C_6$ normal paraffins. The term "rich" is defined to mean a stream having more than 50% of the mentioned component. In addition, the feedstock will include significant amounts of benzene. In order to realize the advantages of this invention, the concentration of benzene in the feedstock will usually at least equal 2 mol % and more typically will reach levels of at least 5 mol %. The benzene content will normally fluctuate from the lower minimum level to much higher levels. In order to obtain the benefits of this invention, the concentration of benzene will usually fluctuate to levels of at least over 5 mol % and more preferably at least 10 mol %. Accordingly, the benzene content of the feed will normally be in a range of from 2 to 25 mol %. There is no upper limit on the concentration of benzene, the maximum benzene content is dictated by the need to have sufficient paraffinic hydrocarbons present for the isomerization reaction. Other feed components will usually comprise $C_5$–$C_6$ cyclics.

The benzene saturation zone of this invention contacts the feed with a hydrogenation catalyst. The benzene saturation will typically reduce the concentration of benzene originally present in the feed stream to at least less than 2 mol %. When feed entering the saturation zone begins with a relatively low benzene concentration on the order of 5 mol % or less the saturation will typically produce an effluent having a benzene concentration of less than 0.1 wt %. The saturation zone will typically comprise a fixed bed of catalyst for promoting the hydrogenation of benzene. Suitable hydrogenation catalysts will provide a metallic function to promote hydrogen transfer without any substantial acid function that would lead to undesirable cracking. Preferred catalyst compositions will include platinum group, tin or cobalt and molybdenum metals on suitable refractory inorganic oxide supports such as alumina. The alumina is preferably an anhydrous gamma-alumina with a high degree of purity. The term platinum group metals refers to noble metals excluding silver and gold which are selected from the group consisting of platinum, palladium, germanium, ruthenium, rhodium, osmium, and iridium. Many of the catalyst that are suitable for the saturation zone can be used in the isomerization zone; thus, the saturation catalyst and the isomerization catalyst can be the same.

Such catalysts will provide satisfactory benzene saturation at the operating conditions of this invention. The operating conditions include temperatures of from 250° F. to 600° F., preferably from 325° F. to 400° F., pressures of from 150 to 900 psig, preferably from 250 to 500 psig, and a 0.5 to 20 liquid hourly space velocity (LHSV), preferably from 1 to 10.

One catalyst for the saturation zone comprises a platinum metal on an alumina support. In its preferred form the alumina support will comprise spheres having a nominal diameter of about 1/16" and surface area of from about 160 to 200 m²/g with an apparent bulk density of from about 0.45 to 0.6 gm/cc. Platinum metal may be present on the catalyst in a concentration of from 0.1 to 1 wt % and preferably in a concentration of from 0.375 to 0.75 wt %.

Chlorided platinum alumina catalysts when used in the saturation or the isomerization zone catalyst are often sulfur and water sensitive. Suitable guard beds or adsorptive separation processes may be used to reduce the sulfur concentration of the feedstock. Preferably the sulfur in the feed to the saturation zone will have a sulfur concentration of less than 0.1 ppm. The sulfur concentration to most isomerization zones should be reduced to less than 0.5 ppm. The presence of sulfur in the feedstock serves to temporarily deactivate platinum type catalysts by platinum poisoning. Activity of the catalyst may be restored by hot hydrogen stripping of sulfur from the catalyst composite or by lowering the sulfur concentration in the incoming feed to below 0.5 ppm 5 so that the hydrocarbon will desorb the sulfur that has been adsorbed on the catalyst. Water, however, can act to permanently deactivate the catalyst by removing high activity chloride from the catalyst and replacing it with inactive aluminum hydroxide. Therefore, water, as well as oxygenates, in particular $C_1$–$C_5$ oxygenates, that can decompose to form water, can only be tolerated in very low concentrations. In general, this requires a limitation of oxygenates in the feed to about 0.1 ppm or less. Sulfur may be removed from the feedstock by hydrotreating. When chlorided platinum alumina catalysts are used, the water content is usually kept within acceptable levels by passing feed that enters the isomerization zone or saturation zone, including any added hydrogen, through a drying zone. The drying zone for this purpose may be of any design that will reduce water content to 0.1 ppm or less. Adsorption processes for the removal of sulfur and water from hydrocarbon streams are also well known to those skilled in the art.

Particularly preferred catalysts for both the saturation reaction zone and the isomerization zone are generally referred to as super acid catalysts. A particularly preferred super acid is a sulfated zirconia. Super acid catalyst compositions including the incorporation of Group VII metal modifiers are well known and described in U.S. Pat. Nos. 5,036,035; 5,157,199; and 4,956,519. Suitable operating conditions for the saturation reaction with sulfated zirconia catalysts include temperatures of from 250° F. to 450° F., preferably from 325° F. to 400° F., pressures of from 150 to 900 psig, preferably from 250 to 600 psig, and a 0.5 to 20 liquid hourly space velocity (LHSV), preferably from 1 to 10.

A hydrogen stream is combined with the saturation zone feedstock to provide hydrogen for hydrogenation in the saturation reactor and the downstream isomerization zone. The amount of hydrogen admixed with the feedstock will vary with the feedstock composition and its stoichiometric feed requirements. At minimum, the hydrogen to hydrocarbon ratio must supply the stoichiometric requirements for the saturation reaction. Although no net hydrogen is consumed in the isomerization reaction, the isomerization zone will have a net consumption of hydrogen often referred to as the stoichiometric hydrogen requirement which is associated with a number of side reactions that occur. These side reactions include saturation of olefins and any remaining aromatics, cracking and disproportionation. Hydrogen concentrations can vary to produce anywhere from a 0.01 to a 10 hydrogen to hydrocarbon ratio in the isomerization zone effluent. Preferably the hydrogen to hydrocarbon ratio in the feed to the saturation zone is minimized to avoid an excess amount of hydrogen exiting with the effluent from the saturation zone. Hydrogen will usually be mixed with the feedstock in an amount sufficient to create a combined feed having a hydrogen to hydrocarbon ratio of from 0.05 to 5. Low hydrogen to hydrocarbon ratios in the combined feed can simplify or eliminate the systems and equipment associated with the addition of hydrogen. Reducing the hydrogen to hydrocarbon ratio at the outlet of the isomerization zone can permit operation the process without the recovery and recycle of hydrogen. At higher hydrogen to hydrocarbon ratios facilities for the recovery of hydrogen from the effluent are needed to prevent the loss of product and feed components that can escape with the flashing of hydrogen from the isomerization zone effluent.

When operating with low hydrogen addition, any suitable means for maintaining the hydrogen addition at or near stoichiometric requirements can be used. Suitable methods include on line analysis of benzene concentration in the input or effluent of the isomerization zone with manual or automatic control of the hydrogen addition rate to the feedstream.

A variety of the saturation catalysts will also promote the opening of saturated hydrocarbon rings. The chlorided platinum alumina catalyst and the sulfated zirconia catalyst in particular have been found to have excellent ring opening activity. Opening of the cyclohexane rings provides additional feed components for skeletal isomerization in the isomerization zone. The saturation and opening of the saturated cyclic hydrocarbons results in a decreased density of the resulting hydrocarbons and an advantageous increase in volumetric product yield. Decyclization is preferably performed in the saturation reaction zone where the higher temperatures that are usually required for ring opening may be employed without adversely affecting equilibrium in the downstream isomerization.

The saturation reaction zone may also provide some isomerization of the incoming feed components. Conditions within the saturation zone will generally employ temperatures that are not optimum for isomerization. Nevertheless when the saturation catalyst is also an isomerization catalyst, some initial isomerization can also take place in the isomerization zone.

At least partially saturated feed from the saturation zone enters the isomerization zone for the rearrangement of the paraffins contained therein from less highly branched hydrocarbons to more highly branched hydrocarbons. The isomerization zone uses a solid isomerization catalyst to promote the isomerization reaction. If there are any unsaturated compounds that enter the isomerization zone after passage through the hydrogenation zone, these residual amounts of unsaturated hydrocarbons will be quickly saturated in the isomerization zone.

There are a number of different isomerization catalysts that can be used for this purpose. One general class of isomerization catalysts use a noble metal as a catalytic component. This noble metal, usually platinum, is utilized on a chlorided alumina support. Another type of catalyst is present on a crystalline alumina silicate support that is typically diluted with an inorganic binder. Preferably, the crystalline alumina type support is a zeolite support and more preferably a mordenite type zeolite. The zeolite type isomerization catalysts are well known and are described in detail in U.S. Pat. Nos. 3,442,794 and 3,836,597.

The chlorided catalyst preferably incorporates a platinum metal on an anhydrous gamma-alumina having a high degree of purity. The catalyst may also contain other platinum group metals. The term platinum group metals refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt. % of the platinum. Other platinum group metals may be present in a concentration of from 0.1 to 0.25 wt. %. The platinum component may exist within the final catalytic composite as an oxide or halide or as an elemental metal. The presence of the platinum component in its reduced state has been found most suitable for this process.

The isomerization catalyst also contains a chloride component. The chloride component termed in the art "a combined chloride" is present in an amount from about 2 to about 10 wt. % based upon the dry support material. The use of chloride in amounts greater than 5 wt. % have been found to be the most beneficial for the isomerization process. As mentioned previously chlorided platinum alumina dehydrogenation and isomerization catalysts are sulfur sensitive and steps for removal of sulfur, water and water precursors such as oxygenates will usually accompany their use.

Another class of catalysts that are particularly preferred for the isomerization zone of this invention are the previously referred to super acid catalysts. These catalysts are generally described in the previously mentioned references. Again, the preferred super acid catalyst for this invention is a sulfated zirconia catalyst. Unlike the chloride platinum alumina catalyst systems, the sulfated zirconia can operate acceptably in the presence of sulfur concentrations of up to 100 ppm and should operate in the presence of water in a concentration of from 1 to 100 ppm. Preferably the sulfur concentration is less from 0 to 5 ppm and the water concentration is in a range of from 5 to 25 ppm.

Operating conditions within the isomerization zone are selected to maximize the production of isoalkane products from the feed components. Temperatures within the reaction zone will usually range from about 105–600° F. (40–315° C.). Lower reaction temperatures are preferred for purposes of isomerization conversion since they favor isoalkanes over normal alkanes in equilibrium mixtures. The isoalkane product recovery can be further increased by opening additional cyclohexane rings produced by the saturation of the benzene. However, if it is desired, maximizing ring opening usually requires temperatures in excess of those that are most favorable for the isomerization reaction from an equilibrium standpoint. For example, when the feed mixture is primarily $C_5$ and $C_6$ alkanes, temperatures in the range of 140–320° F. (60–160° C.) are desired from a normal-isoalkane equilibrium standpoint, in order to achieve significant opening of $C_5$ and $C_6$ cyclic hydrocarbon rings, the preferred temperature range for this invention lies between 325–400° F. (165–205° C.). When it is desired to also isomerize significant amounts of $C_4$ hydrocarbons, higher reaction temperatures are required to maintain catalyst activity. Thus, when the feed mixture contains significant portions of $C_4$–$C_6$ alkanes, the most suitable operating temperatures for ring opening and isoalkane equilibrium coincide and are in the range from 290–440° F. (145–225° C.). The reaction zone may be maintained over a wide range of pressures. Pressure conditions in the isomerization of $C_4$–$C_6$ paraffins range from 150 to 900 psig. The feed rate to the reaction zone can also vary over a wide range. These conditions include liquid hourly space velocities ranging from 0.5 to 20 hr.$^{-1}$, however, space velocities between 0.5 and 10 hr.$^{-1}$ are preferred.

Operation of the reaction zone with the chlorided platinum alumina catalyst also requires the presence of a small amount of an organic chloride promoter. The organic chloride promoter serves to maintain a high level of active chloride on the catalyst as small amounts of chloride are continuously stripped off the catalyst by the hydrocarbon feed. The concentration of promoter in the reaction zone is usually maintained at from 30 to 300 ppm. The preferred promoter compound is carbon tetrachloride. Other suitable promoter compounds include oxygen-free decomposable organic chlorides such as propyldichloride, butylchloride, and chloroform to name only a few of such compounds. The need to keep the reactants dry when employing the chlorided platinum alumina type catalyst is reinforced by the presence of the organic chloride compound which may convert, in part, to hydrogen chloride. As long as the process streams are kept dry, there is no adverse effect from the presence of small amounts of hydrogen chloride.

In the arrangement of this invention, the saturation zone is placed upstream of a downstream isomerization zone. Preferably, all of the effluent from the saturation zone passes directly to the isomerization zone. For benzene concentrations of less than about 2 wt % benzene, the flow path for the benzene containing isomerization feed takes an ordinary flow path where the reactants pass first through a heat exchanger to recover heat from the effluent and then serially through the saturation reaction zone and the isomerization reaction zone.

It is anticipated that in many arrangements for this invention, the isomerization zone effluent will pass from the feed heat exchanger to a separator for the recovery and recycle of hydrogen with the separator bottoms passing to a stabilizer for the removal of additional light ends and the recovery of an isomerization output stream. At minimum, the separation facilities divide the reaction zone output into a product stream comprising $C_5$ and heavier hydrocarbons and a gas stream which is made up of $C_3$ lighter hydrocarbons and hydrogen. Suitable designs for rectification columns and separator vessels to separate the isomerization zone effluent are well known to those skilled in the art.

While benzene concentrations are low, below about 2 wt % temperatures within the saturation zone and the isomerization reaction zone are controlled by adjusting the heat input by feed heater. As the amount of benzene in the feed input to the process increases above about 2 wt %, heat generated by the saturation of additional amounts of benzene is offset through the by-passing of feed around the heat exchanger that indirectly exchanges heat from the isomerization zone output stream with the feedstream. Feed heater temperatures are also reduced as the by-passing is continued to shift heat input from the heater to the saturation zone. The entering temperature for the saturation zone feed to initiate the saturation reaction will vary depending on the catalyst used. Generally, the saturation reaction zone will operate with an initial temperature of 200 to 350° F. A small amount of heat exchange is usually maintained between the isomerization zone output stream and the saturation zone feed to maintain the desired temperature at the inlet of the saturation zone. Temperatures at the inlet to the isomerization zone are generally kept below 350° F. and usually within a range of 250 to 350° F.

As the amount of benzene in the feedstream continues to increase, further by-passing and reductions in heater input can not offset the heat input from the saturation zone while maintaining a suitable inlet temperature to the saturation zone. The recycle of the quench material directly upstream of the isomerization zone with the saturation zone effluent further controls the temperature of reactants at the inlet to the isomerization zone. The process uses a quench that includes at least a portion of an internal stream obtained by splitting the feed to the saturation zone or splitting the bottom stream from a hydrogen separator. The quench stream is charged directly to the isomerization zone when the intermediate feed stream passing to the isomerization zone exceeds 400° F. The quench portion of the feedstream or the separator bottoms stream are charged to the inlet of the isomerization zone. The quench stream can comprise a portion of both the feedstream and the separator bottoms stream. Unless otherwise noted the term "portion" in this specification when describing a process stream refers to either an aliquot portion of the stream or a dissimilar fraction of the stream having a different composition than the total stream from which it was derived. The quench stream may be at least partially liquid phase to provide cooling from latent heat effects.

In order to minimize the additional mass volume through the isomerization zone, charging a portion of the saturation zone feed directly to the isomerization zone is preferred since it reduces total mass flow through the reaction zones. Therefore, to the extent that additional benzene can be tolerated in the product specification or the isomerization section can provide the additional necessary benzene saturation, it is preferred to quench the intermediate stream entering the isomerization zone directly with a portion of the saturation zone feedstream.

Through a combination of feed and separator bottoms recycled, this invention provides the flexibility to reduce the benzene concentration as necessary to meet product specifications while accommodating feeds that have a widely varying concentration of benzene. For example, when the benzene concentration exceeds 5 wt %, the process can be operated by using high severity conditions in the benzene saturation zone and an exclusive use of quench material from the product separator such that the isomerization zone effluent is completely saturated.

Where higher concentrations of benzene are permitted in the product specification, severity within the saturation zone may be reduced to further control temperatures or more of the feed can be directly charged to the isomerization zone as a quench material to reduce total mass flow through the saturation and isomerization zones. The separator bottoms contain the most highly saturated hydrocarbon stream and its recycle to the isomerization reaction zone will not increase the benzene concentration in the final isomerization zone effluent. Therefore, to the extent that additional mass flow through the isomerization zone is possible, the recycle of separator bottom streams will provide the necessary quench without increasing the benzene concentration in the final isomerization zone effluent.

Figure 1:
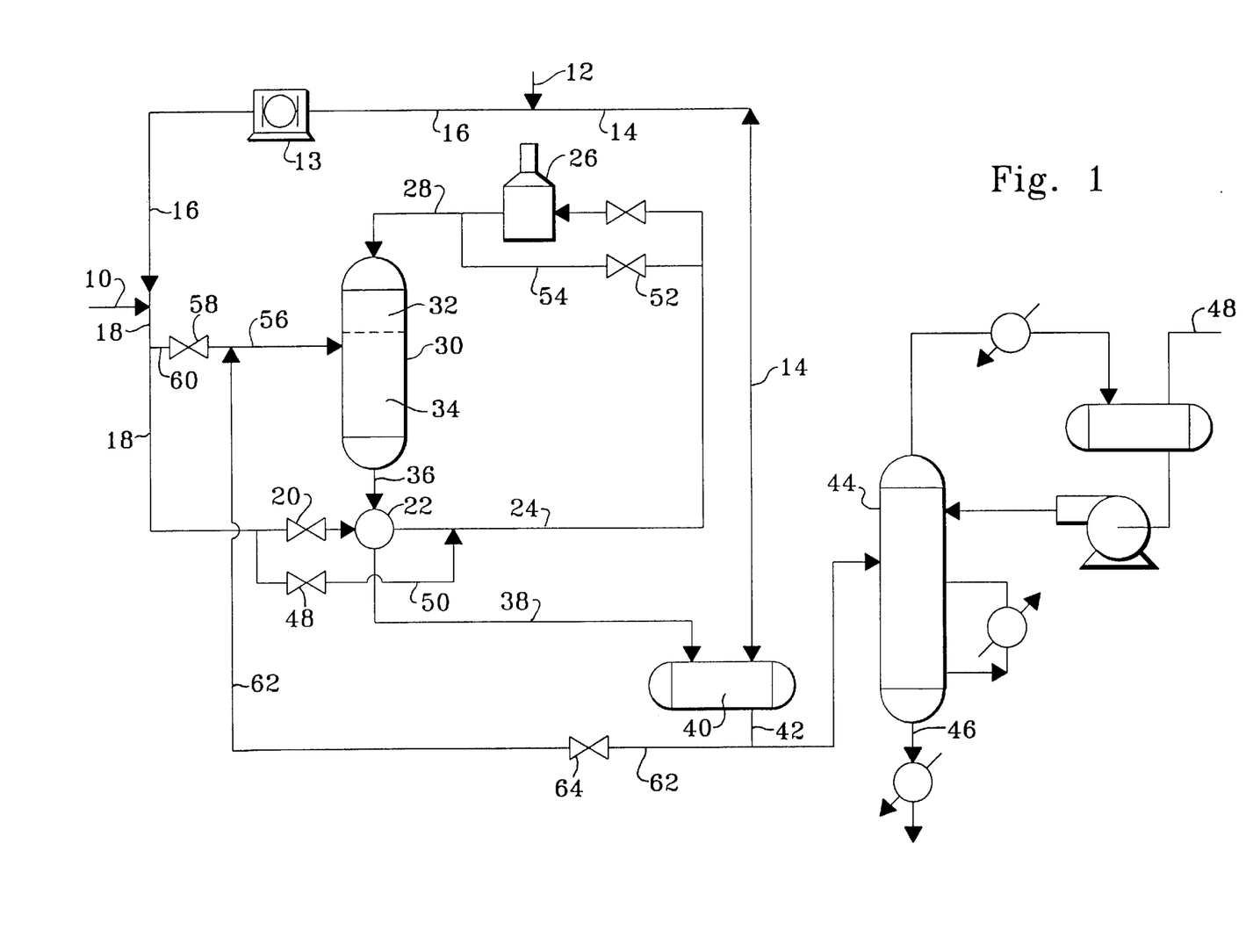
FIG. 1 shows a preferred arrangement for the benzene saturation process of this invention.

A basic arrangement for the processing equipment used in this invention can be readily understood by a review of the flow scheme presented in FIG. 1. FIG. 1 and this description makes no mention of many pumps, compressors, receivers, condensers, reboilers, instruments, and other well known items of processing equipment in order to simplify the explanation of the invention.

Looking then at FIG. 1, an isomerization zone feed made up of $C_4$–$C_6$ normal paraffins and 2 wt % benzene enters the process via a line 10. The feed enters the process at a temperature of about 100° F. Makeup hydrogen enters the process through line 12 and is admixed with recycle hydrogen carried by line 14. Makeup and recycled hydrogen passes via a line 16 through a recycle compressor 13 and into admixture with the incoming feedstream. Line 18 carries the feedstream across a control valve 20 and a combined feed heat exchanger 22. The passage of the feed through exchanger 22 raises its temperature to about 320° F. Heated feed from exchanger 22 is carried by line 24 to a feed heater 26. Feed heater 26 heats the feed carried by a line 28 to the saturation reaction zone inlet temperature. Line 28 passes the total feed to the saturation zone from heater 26 at a temperature of about 350° F. The heated feed enters an upper part of a reaction vessel 30 that contains a saturation reaction zone 32. The saturation zone performs an essentially complete saturation of the benzene components. Saturated feed from saturation reaction zone 32 passes downwardly into an isomerization reaction zone 34. The isomerized and saturated feed passes via a line 36 through combined feed exchanger 22 to cool the isomerization zone output stream which passes via a line 38 into a separator 40. The hydrogen containing gas stream is recovered from the separator by a line 14 and the separated isomerization zone liquid passes via a line 42 to a stabilizer 44. Stabilizer 44 separates the isomerization zone output stream into an isomerization zone effluent stream taken from the stabilizer via a line 46 and a net gas overhead stream taken via line 48.

As the concentration of benzene entering via line 10 increases, a valve 48 is opened on a by-pass line 50 to allow a portion of the combined feed to by-pass the combined feed exchanger 22.

The by-pass feed is recombined with the remainder of the feed that passes through exchanger 22 to produce a benzene feed having an average temperature of 308° F. which is carried by line 24. A control valve 52 is opened completely to by-pass the heated feed around heater 26 via a line 54. Line 28 carries the saturation feed into the saturation zone. The intermediate feed from the saturation zone again passes through the isomerization zone and through the separator and stabilizer sections for recovery of hydrogen and the isomerate product.

As the concentration of benzene in the entering feed increases to a concentration of about 5 wt %, only a portion of the feed to the process passes through line 18. The portion of the feed carried by line 18 is again by-passed around heat exchanger 22 via line 50. A sufficient amount of the feedstream is by-passed to maintain only a minimum inlet temperature for the saturation reaction zone. The feed from line 24 continues to by-pass heater 26 via line 54 and 28. An intermediate stream again passes out of saturation zone 32. The intermediate stream is mixed with a quench stream 56 that is injected directly into reactor vessel 34 between the saturation zone 32 and the isomerization zone 34. The quench stream is a mixture of the saturation zone feed taken from line 18 via a line 60 at a rate controlled by a control valve 58 and a portion of the separator bottoms diverted from line 42 via a line 62 at a rate regulated by a control valve 64. The combined quench stream has a temperature of about 108° F. and is admixed in a 1:1 weight ratio to the intermediate stream passing into the isomerization zone. The input of the quench lowers the temperature of the intermediate stream to an average temperature of about 290° F. at the inlet to the isomerization zone. The portion of the feed that passes as a quench to the intermediate stream entering the isomerization reaction zone raises the benzene concentration at the inlet to about 6 wt %. Additional benzene that enters the isomerization zone with the quench material is saturated in the isomerization reaction zone so that an isomerate having a benzene concentration of less than 0.1 wt % is recovered from stabilizer 44 via line 46.

The picture and description of the process in FIG. 1 shows a preferred arrangement for the benzene saturation zone and isomerization zone where both zones are located in a single reaction vessel. The invention may also be practiced with the isomerization zone and saturation zone in separate vessels. In a separate vessel arrangement for the benzene and isomerization catalyst bed, quench may be injected into the process at any point that would serve to effectively lower the temperature of the reactants ahead of the isomerization zone. For example the quench may be injected into a transfer line that passes the intermediate stream from the benzene saturation zone to the isomerization zone. That portion of the quench that is taken from the stabilizer and has a low benzene concentration may be injected directly into an intermediate section of the saturation zone to reduce temperatures in the saturation zone as well as the isomerization zone.

Figure 2:
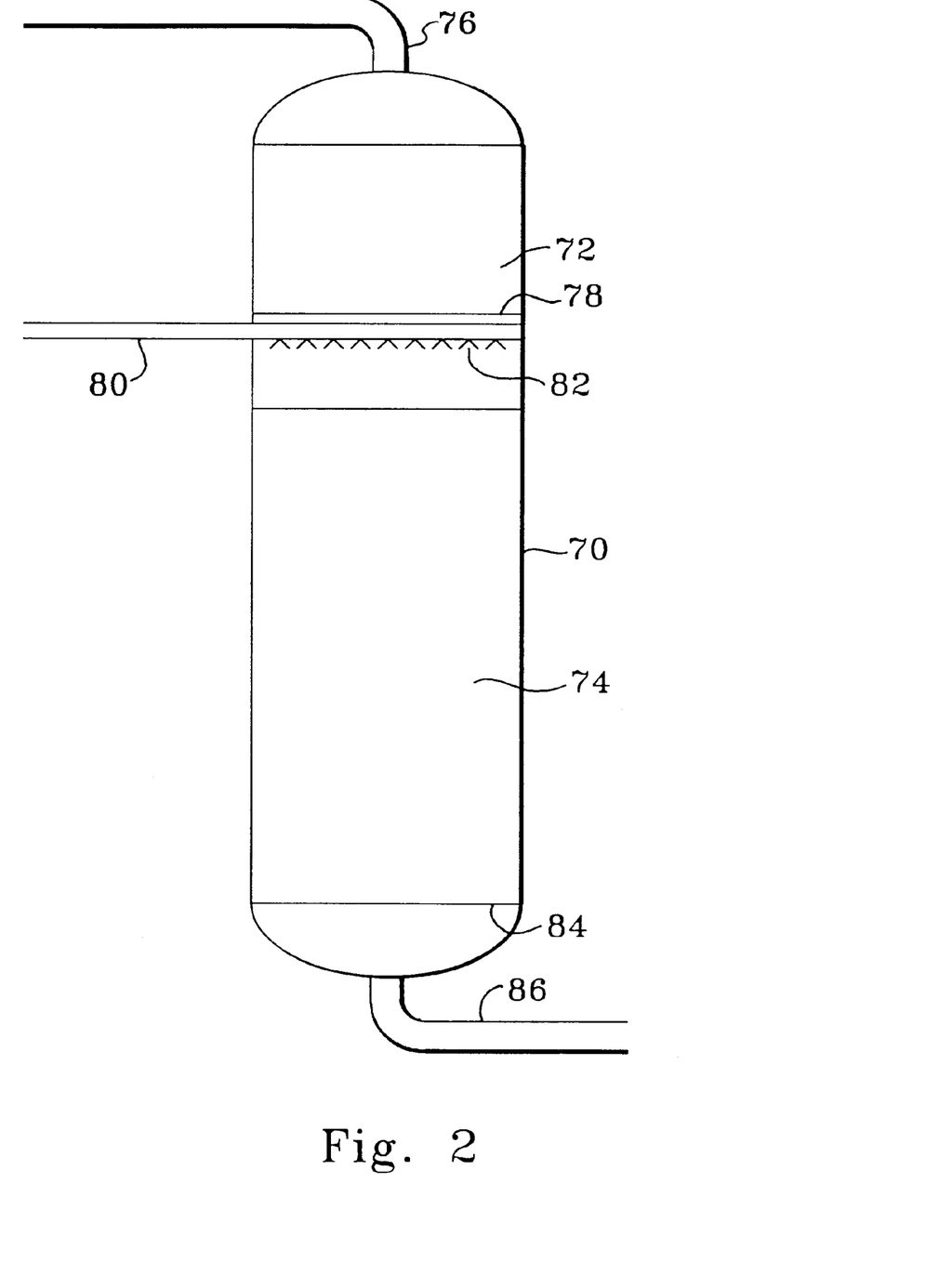
FIG. 2 is a schematic diagram of the preferred internal arrangement for the reactor of this invention.

FIG. 2 shows this arrangement wherein a reactor vessel 70 is divided into an upper isomerization zone 72 that retains a benzene saturation zone in a fixed catalyst bed. The lower part of reactor vessel 70 defines a catalyst bed 74 that retains a fixed bed of isomerization catalyst. The saturation zone feed enters the top of reactor vessel 70 through an inlet line 76. Entering saturation zone feed may be distributed across the top of bed 72 by the use of a feed distributor. Suitable feed distributors to distribute feed across the surface of a fixed catalyst bed are known by those skilled in the art. After reaction in bed 72, the converted feed containing saturated feed components passes out of bed 72 across a catalyst support grid 78. The quench stream enters the process via a line 80 and is distributed across the cross section of the reactor by a distributor 82. As the saturation zone effluent flows across grid 78, it is intimately mixed with the quench stream. The mixture of additional feed and quench components flows through bed 74, across a support grid 84, and out of reactor vessel 70 via a line 86.

The use of a sulfated zirconia catalyst makes it possible to utilize the preferred single reactor vessel arrangement of FIG. 2 in existing isomerization processes. Compared to zeolitic catalyst, the sulfated zirconia has about an 80 % increase in density compared to typical zeolitic isomerization catalyst. Other typical isomerization catalyst have an apparent bulk density of about 0.65 gm/cc. Extruded sulfated zirconia catalyst will typically have an apparent bulk density of about 1.2 gm/cc. As a result, a bed of sulfated zirconia catalyst can occupy almost half as much space as a traditional isomerization zone catalyst while still providing the same degree of activity. Therefore, the dual saturation zone and isomerization zone beds of this invention can be incorporated into a single isomerization zone by using the sulfated zirconia catalyst which only needs a little more than half of the available bed area that was previously used. The new open area of the bed provides available volume for the incorporation of the upstream benzene saturation zone.

Therefore, an existing isomerization zone reactor vessel is easily converted to the process of this invention by partitioning a reactor vessel into an upper saturation zone and a lower isomerization zone. A quench injection is provided between the upper saturation zone and the lower isomerization zone. The remaining equipment of the process may also be converted by providing a by-pass for the indirect heat exchange of a portion of the feedstream such that a portion of the saturation zone feed can enter the saturation zone without indirect heat exchange. It is also a relatively simple matter to provide the necessary lines for passing a portion of the feed to the isomerization zone at the quench location and returning a portion of the isomerization zone output stream directly to the isomerization zone at the quench location.

In order to more fully illustrate the process, the following example is presented to demonstrate the ability of a sulfated zirconia catalyst to provide isomerization in the presence of benzene and cyclic hydrocarbons.

EXAMPLE

Figure 3:
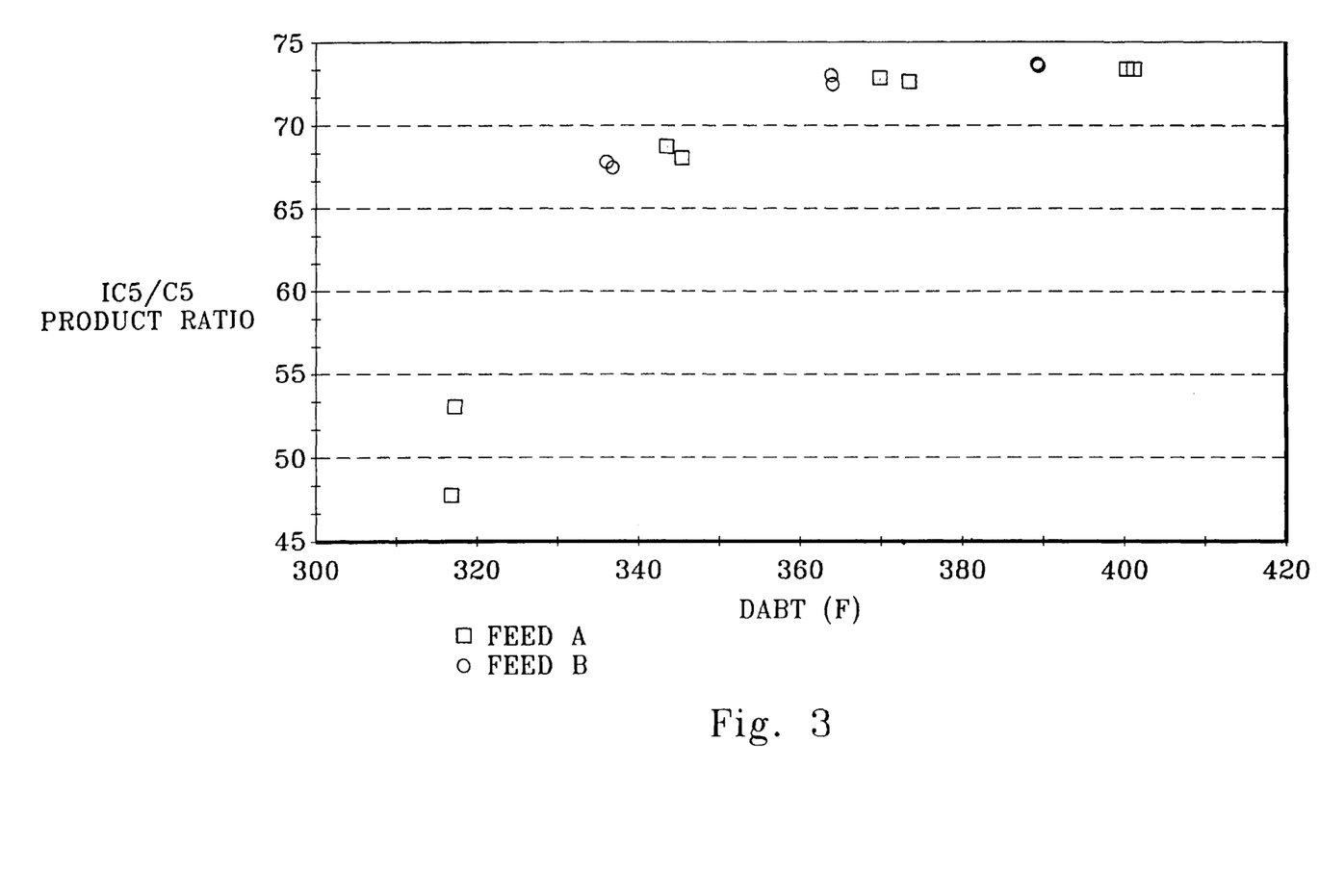
FIGS. 3 and 4 are graphs showing the performance of the preferred sulfated zirconia catalyst.
Figure 4:
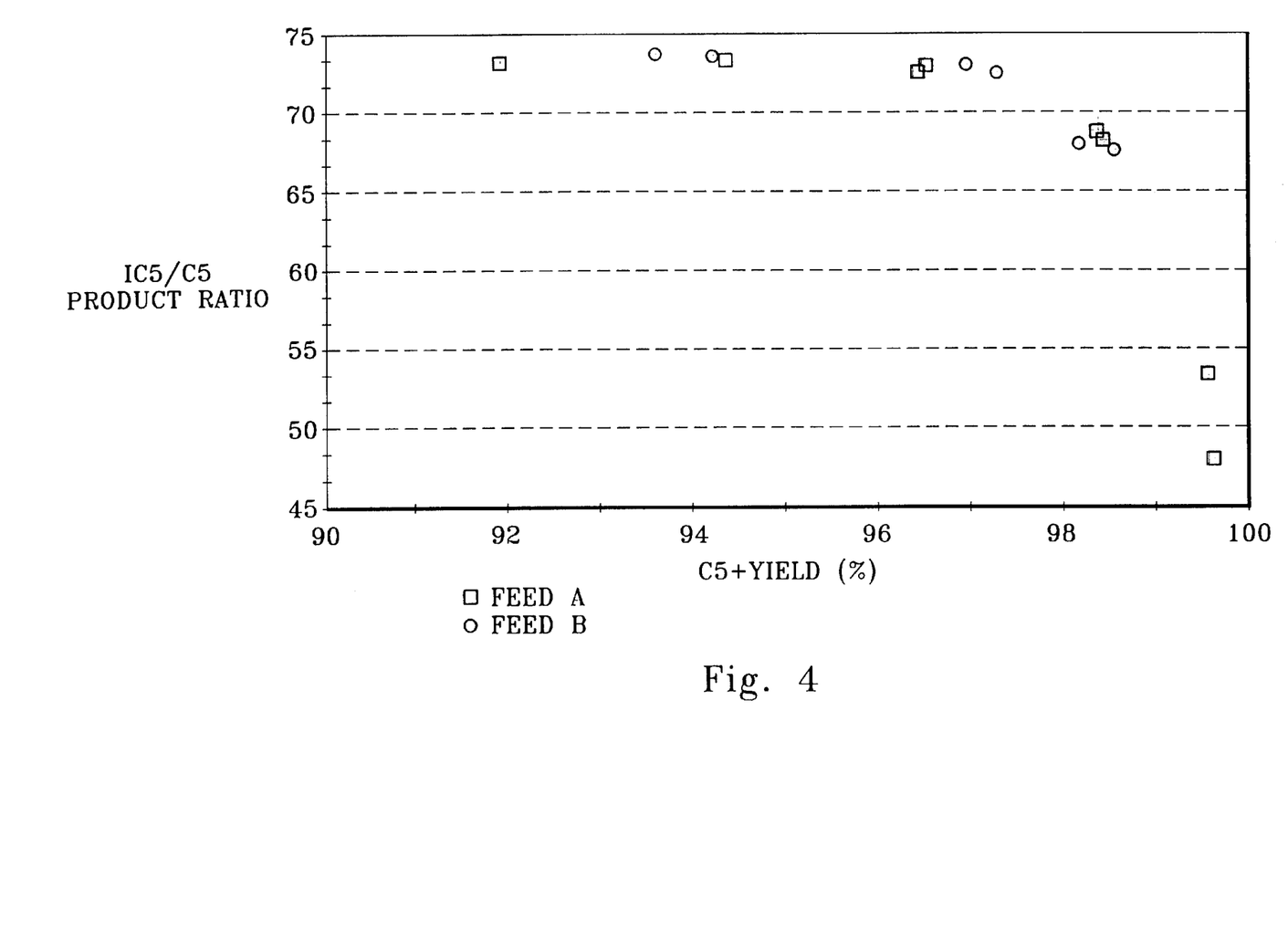

A sulfated zirconia catalyst containing about 90 wt % sulfated zirconia and 0.36 wt % Pt was bound in about 10 wt % of an alumina binder. The catalyst was contacted with two feeds over a range of operating temperatures. The compositions of the feeds are given in the Table. Feed A contained about 3.6 wt % benzene, 1.8 wt % $C_6$ saturated cyclic hydrocarbons with the remainder of the feed comprising $C_5$ and $C_6$ normal paraffins. Feed B contained about 6.0 wt % $C_6$ saturated cyclic hydrocarbons with the remainder of the feed comprising $C_5$ and $C_6$ normal paraffins. Both feeds were combined with hydrogen in a ratio of hydrogen to hydrocarbons of 2 and contacted with the catalyst at 450 psig and a weight hourly space velocity of 1.55 $hr^{-1}$. The conversion as a function of average bed temperature and yield are shown in FIGS. 3 and 4. The data plotted in the figures demonstrate the sulfated zirconia catalyst will provide high conversion of normal pentanes to isopentanes in the presence of both benzene and cyclic hydrocarbons.

Complete saturation of the benzene was achieved at all bed temperatures.

TABLE

| COMPONENT | FEED A | FEED B |
|---|---|---|
| ISOPENTANE | 0.15 | 0.21 |
| n-PENTANE | 46.72 | 45.25 |
| CYCLOPENTANE | 0.06 | 0.03 |
| 23 DIMETHYLBUTANE | 0.01 | 0.02 |
| 2 METHYLPENTANE | 0.00 | 0.00 |
| 3 METHYLPENTANE | 0.09 | 0.08 |
| n-HEXANE | 46.89 | 48.91 |
| METHYLCYCLOPENTANE | 0.97 | 1.26 |
| BENZENE | 0.00 | 3.59 |
| CYCLOHEXANE | 5.01 | 0.62 |
| C7+ | 0.10 | 0.06 |
| TOTAL CYCLICS | 5.98 | 5.46 |

What is claimed is:

1. A process for the hydrogenation of benzene and the isomerization of $C_4$ to $C_6$ paraffins, said method comprising:
    a) passing at least a portion of a feedstream comprising benzene and $C_4$ to $C_6$ normal paraffins and a hydrogen containing stream to a benzene saturation zone and into contact with a benzene saturation catalyst at benzene saturation conditions to produce an intermediate stream comprising cyclohexane and $C_4$ to $C_6$ normal paraffins;
    b) passing said intermediate stream to an isomerization zone and contacting said intermediate stream with an isomerization catalyst at isomerization conditions to increase the isoparaffin content of said intermediate stream and producing an isomerization zone output stream;
    c) passing a quench stream comprising at least a portion of one of said feedstream or said output stream directly into said isomerization zone when the benzene content of said feedstream exceeds about 5 wt %; and,
    d) recovering an isomerization effluent stream comprising at least a portion of said output stream.

2. The process of claim 1 wherein the benzene content of said feedstream fluctuates from 2 to 30 wt %.

3. The process of claim 1 wherein said isomerization output stream passes in indirect heat exchange with the portion of said feedstream entering said saturation reaction zone to heat the portion of said feedstream entering said saturation reaction zone and a portion of said feedstream by passes said indirect heat exchange and directly enters said saturation reaction zone.

4. The process of claim 1 wherein said quench stream passes directly to said isomerization zone when said intermediate stream is above a temperature of at least 400° F.

5. A process for the hydrogenation and decyclization of benzene and the isomerization of C4 to C6 paraffins from a hydrocarbon feedstream having a concentration of benzene that fluctuates between above and below 5 wt %, said method comprising:
 a) passing at least a portion of a feedstream comprising benzene and $C_4$ to $C_6$ paraffins and a hydrogen containing stream to a benzene saturation zone and into contact with a benzene saturation catalyst at benzene saturation conditions to produce an intermediate stream containing cyclohexane;
 b) passing said intermediate stream to an isomerization zone inlet and contacting said intermediate stream with and isomerization catalyst at isomerization conditions in said isomerization zone to decyclize said cyclohexane, increase the isoparaffin content of said intermediate stream and produce an isomerization zone output stream;
 c) passing at least a portion of said isomerization zone output stream into indirect heat exchange with a portion of the feedstream entering said saturation zone;
 d) passing said isomerization zone output stream to a separator to recover hydrogen and an isomerization zone effluent stream and recycling at least a portion of said hydrogen to said saturation zone;
 e) maintaining the temperature at the inlet of said isomerization zone below 350° F. by charging a portion of said feedstream directly to said saturation zone without said intermediate heat exchange as long as said benzene concentration in said feedstream is below 5 wt % and passing a quench stream comprising at least a portion of one of said feedstream or said isomerization zone effluent stream directly into said isomerization zone when the benzene content of said feedstream exceeds 5 wt %.

6. The process of claim 5 wherein the temperature at the inlet of said isomerization zone is maintained at temperature of 250 to 350° F.

\* \* \* \* \*